(12) United States Patent
Harding et al.

(10) Patent No.: US 8,197,452 B2
(45) Date of Patent: Jun. 12, 2012

(54) VASCULAR ACCESS DEVICE NON-ADHERING SURFACES

(75) Inventors: Weston F. Harding, Lehi, UT (US);
Austin Jason McKinnon, Herriman, UT (US); Mark A. Crawford, Sandy, UT (US); Lantao Guo, Draper, UT (US); Glade H. Howell, Sandy, UT (US); David Ou-Yang, Woodbury, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 419 days.

(21) Appl. No.: 11/829,006

(22) Filed: Jul. 26, 2007

(65) Prior Publication Data
US 2008/0027400 A1    Jan. 31, 2008

Related U.S. Application Data

(60) Provisional application No. 60/820,653, filed on Jul. 28, 2006.

(51) Int. Cl.
*A61M 5/00* (2006.01)
*A61M 5/178* (2006.01)
*A61M 5/14* (2006.01)
*A61M 25/00* (2006.01)
*A61M 5/32* (2006.01)
*A61M 25/16* (2006.01)
*A61M 25/18* (2006.01)
*A61M 39/00* (2006.01)
*A61M 39/10* (2006.01)
*A61F 7/12* (2006.01)
*A61B 18/14* (2006.01)

(52) U.S. Cl. ........ 604/246; 128/912; 604/113; 604/114; 604/164.01; 604/167.01; 604/167.02; 604/167.03; 604/167.04; 604/256; 604/264; 604/265; 604/523; 604/533; 604/534; 604/535; 604/537; 604/905

(58) Field of Classification Search ............... 251/149.1; 604/265, 246, 256, 905, 252, 406, 533, 167.01, 604/167.02, 167.03, 167.04, 164.01, 167.06, 604/264, 48, 523, 537, 539, 93.01, 113, 114, 604/20, 21, 534, 535; 128/912
See application file for complete search history.

(56) References Cited

U.S. PATENT DOCUMENTS

| | | | |
|---|---|---|---|
| 4,765,588 A | | 8/1988 | Atkinson |
| 4,994,167 A | * | 2/1991 | Shults et al. ............ 204/403.05 |
| 5,251,873 A | | 10/1993 | Atkinson et al. |
| 5,295,657 A | | 3/1994 | Atkinson |
| 5,295,658 A | | 3/1994 | Atkinson et al. |
| 5,342,316 A | | 8/1994 | Wallace |
| 5,441,487 A | | 8/1995 | Vedder |
| 5,474,544 A | | 12/1995 | Lynn |
| 5,501,426 A | * | 3/1996 | Atkinson et al. ........... 251/149.1 |
| 5,533,708 A | | 7/1996 | Atkinson et al. |
| 5,543,111 A | * | 8/1996 | Bridges et al. .................. 422/22 |
| 5,549,651 A | | 8/1996 | Lynn |

(Continued)

*Primary Examiner* — Kevin C Sirmons
*Assistant Examiner* — Shefali Patel
(74) *Attorney, Agent, or Firm* — Mony R. Ghose; Kirton & McConkie

(57) ABSTRACT

A vascular access device may include a body and a layer of the body that communicates with a pathogenic environment to discourage adhesion of a pathogen to the layer and thus repress pathogenic activity. A method of repressing pathogenic activity in a vascular access device includes providing the device with a body, and coating the body with a layer that discourages adhesion of a pathogen to the layer.

12 Claims, 6 Drawing Sheets

U.S. PATENT DOCUMENTS

| | | |
|---|---|---|
| 5,957,898 A | 9/1999 | Jepson et al. |
| 6,017,334 A | 1/2000 | Rawls |
| 6,171,287 B1 | 1/2001 | Lynn et al. |
| 6,261,282 B1 | 7/2001 | Jepson et al. |
| 6,344,033 B1 | 2/2002 | Jepson et al. |
| 6,468,649 B1 | 10/2002 | Zhong |
| 6,595,964 B2 | 7/2003 | Finley et al. |
| 6,651,956 B2 | 11/2003 | Miller |
| 6,669,681 B2 | 12/2003 | Jepson et al. |
| 6,723,350 B2 | 4/2004 | Burrell et al. |
| 6,844,028 B2 | 1/2005 | Mao et al. |
| 6,866,656 B2 | 3/2005 | Tingey et al. |
| 6,908,459 B2 | 6/2005 | Harding et al. |
| 2001/0010016 A1 | 7/2001 | Modak et al. |
| 2002/0102405 A1 | 8/2002 | Chapman et al. |
| 2002/0133124 A1* | 9/2002 | Leinsing et al. .............. 604/256 |
| 2002/0168530 A1* | 11/2002 | Tingey et al. ................. 428/421 |
| 2002/0193752 A1 | 12/2002 | Lynn |
| 2003/0018306 A1 | 1/2003 | Bucay-Couto et al. |
| 2003/0134783 A1 | 7/2003 | Harshey et al. |
| 2004/0106942 A1* | 6/2004 | Taylor et al. .................. 606/185 |
| 2004/0115721 A1 | 6/2004 | Mao et al. |
| 2004/0122511 A1 | 6/2004 | Mangiardi et al. |
| 2004/0188351 A1 | 9/2004 | Thiele et al. |
| 2005/0008671 A1 | 1/2005 | Van Antwerp |
| 2005/0038498 A1 | 2/2005 | Dubrow et al. |
| 2005/0048124 A1 | 3/2005 | Sarangapani |
| 2005/0124970 A1* | 6/2005 | Kunin et al. .................. 604/508 |
| 2005/0154448 A1 | 7/2005 | Cully et al. |
| 2005/0221072 A1 | 10/2005 | Dubrow et al. |
| 2005/0256500 A1 | 11/2005 | Fujii |
| 2006/0150862 A1* | 7/2006 | Zhao et al. .................. 106/286.1 |

* cited by examiner

VASCULAR ACCESS DEVICE NON-ADHERING SURFACES

RELATED APPLICATIONS

This application claims the benefit of U.S. Provisional Application No. 60/820,653, filed Jul. 28, 2006, entitled VASCULAR ACCESS DEVICE NON-ADHERING SURFACES, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The proximal end of the vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes or seals the vascular access device, and allows for intermittent infusion or injection of fluids and pharmaceuticals. An IV access device may include a housing and a septum for closing the system. The septum may be opened with a blunt cannula or a male Luer of a medical device.

Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Vascular access device infection resulting in CRBSIs may be caused by failure to regularly clean the device, a non-sterile insertion technique, or by pathogens entering the fluid flow path through either end of the path subsequent to catheter insertion. Studies have shown the risk of CRBSI increases with catheter indwelling periods. When a vascular access device is contaminated, pathogens adhere to the vascular access device, colonize, and form a biofilm. The biofilm is resistant to most biocidal agents and provides a replenishing source for pathogens to enter a patient's bloodstream and cause a BSI. Thus, what are needed are systems, devices, and methods to reduce the risk and occurrence of CRBSIs.

BRIEF SUMMARY OF THE INVENTION

The present invention has been developed in response to problems and needs in the art that have not yet been fully resolved by currently available vascular access systems, devices, and methods. Thus, these systems, devices, and methods are developed to reduce the risk and occurrence of CRBSIs by providing a vascular access device that prevents or discourages one or more pathogens from adhering to the device. By discouraging pathogen adhesion, the non-adhering device prevents or limits pathogen colonization and proliferation into a biofilm and/or harmful culture.

A vascular access device may include a body and a layer of the body that communicates with a pathogenic environment. The layer discourages adhesion of a pathogen to the layer to repress pathogenic activity.

The layer may include a radio frequency coating that is heated to repress pathogenic activity. The layer may also include a resistive and conductive coating, which may include nickel chrome, for receiving an electric field that is heated by a rapidly oscillating electric field to repress pathogenic activity. The layer may also include glass, ceramic, a small chain polyethylene oxide, polyvinyl alcohol, polylactide, polytetrafluoroethylene, a microsurface of peaks and valleys spaced to repress pathogenic activity, and/or plasma.

A method of repressing pathogenic activity in a vascular access device may include providing a body of the device, and coating the body with a layer that discourages adhesion of a pathogen to the layer. The method may include transmitting radio frequency energy to the layer. The method may include emitting a rapidly oscillating electric field to the layer, where the layer includes nickel chrome. The layer may also include glass, ceramic, a small chain polyethylene oxide, polytetrafluoroethylene, and/or plasma. Coating the body may also include forming a series of microsurface peaks and valleys on the layer.

A medical device may also include means for discouraging adhesion of a pathogen residing near a means for accessing the vascular system of a patient. The means for accessing the vascular system of a patient includes a body, and means for discouraging adhesion of a pathogen includes a layer of the body of the means for accessing the vascular system of a patient.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
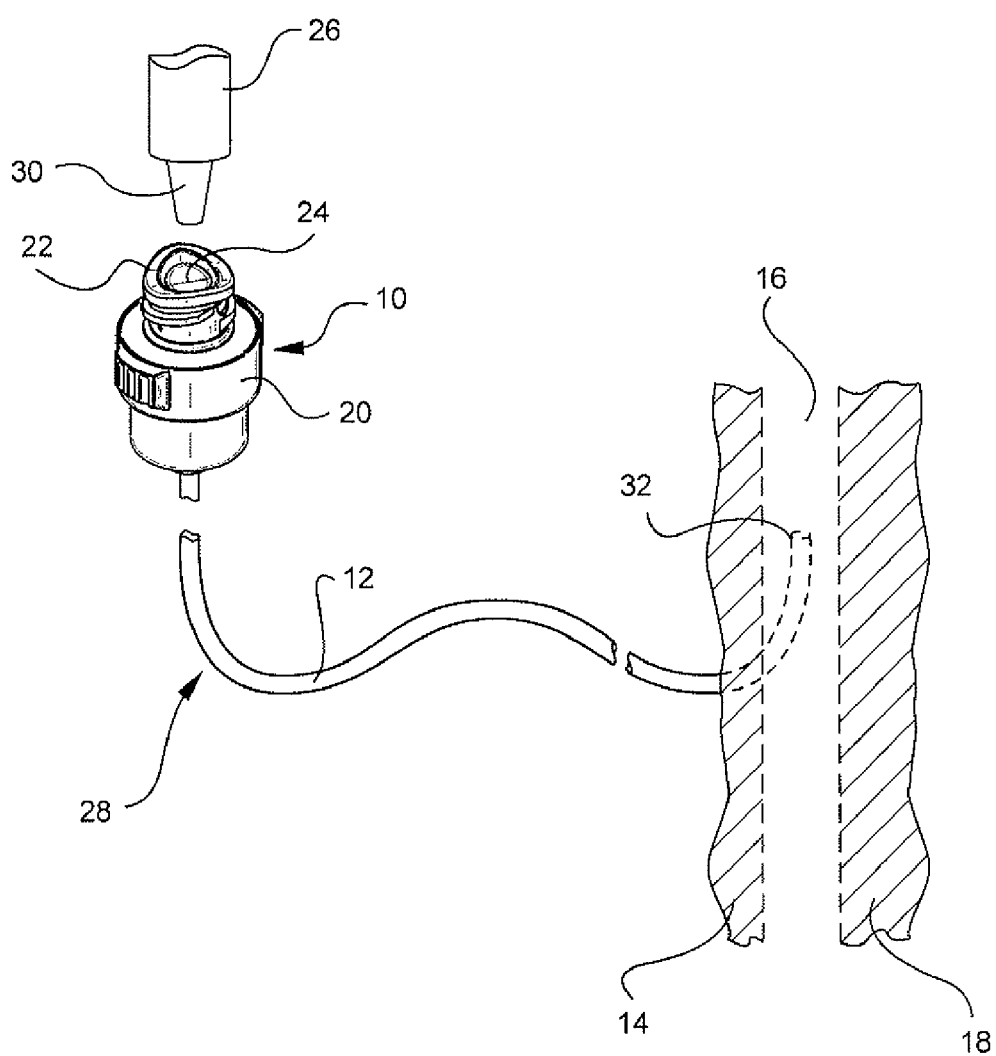
FIG. 1 is a perspective view of an extravascular system connected to the vascular system of a patient.

Referring now to FIG. 1, a vascular access device (also referred to as an extravascular device, intravenous access device, access port, and/or any device attached to or functioning with an extravascular system) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 also includes a layer (discussed with reference to the figures below) integrated or compounded with, in, and/or on the body 20 of the device 10, an extravascular system 28, and/or septum 22. The layer discourages, inhibits, prevents, or otherwise limits a pathogen from adhering to the layer. By discouraging pathogen adhesion, the non-adhering layer on the surface represses the pathogen by preventing or limiting pathogen colonization and proliferation into a biofilm and/or harmful culture. The layer represses at least one pathogen to decrease the incidence of blood stream infections in patients to whom the vascular access device 10 or any other device on the extravascular system 28 is attached.

As described throughout this specification, pathogens include any agent that causes or facilitates a disease, infects, or otherwise harms or has the potential to harm a patient or host if received into the vascular system of that patient or host. A pathogen includes a pathogen, bacterium, parasite, microbe, biofilm, fungus, virus, protein feeding a pathogen, protozoan, and/or other harmful microorganisms and/or agents and products thereof. The layer discourages a pathogen from adhering and/or represses pathogenic activity to prevent the proliferation, growth, or organization of a harmful biofilm by any one or combination of the following actions: removing, dislodging, repelling, resisting, detaching, loosening, unbinding, unfastening, releasing, separating, dividing, disconnecting, and/or freeing a pathogen from a surface of the device 10 and/or any other similar process or action.

A pathogen may enter the device 10 or system 28 in any of a number of ways. For example, a pathogen may reside within the device 10 or system 28 prior to first use. A pathogen may also be introduced into the device 10 from the external surface of the device, the external surface of a separate device 26, and/or the surrounding environment when a structure such as a tip 30 of the separate device 26 is inserted into the device 10 through the slit 24 of the septum 22. A pathogen may be introduced within fluid that is infused into the system from a separate device 26. Finally, a pathogen may be introduced from a blood vessel 16 into the system 28 by entering through the end 32 of the catheter 12 during a blood draw or a period of blood reflux when the device 10 is in use. The layer may thus be integrated, compounded, and/or placed in or on any surface, structure, or body of the entry, junctions, and/or fluid path of the system 28 in order to discourage pathogen adhesion and repress pathogenic activity, as desired.

Figure 2:
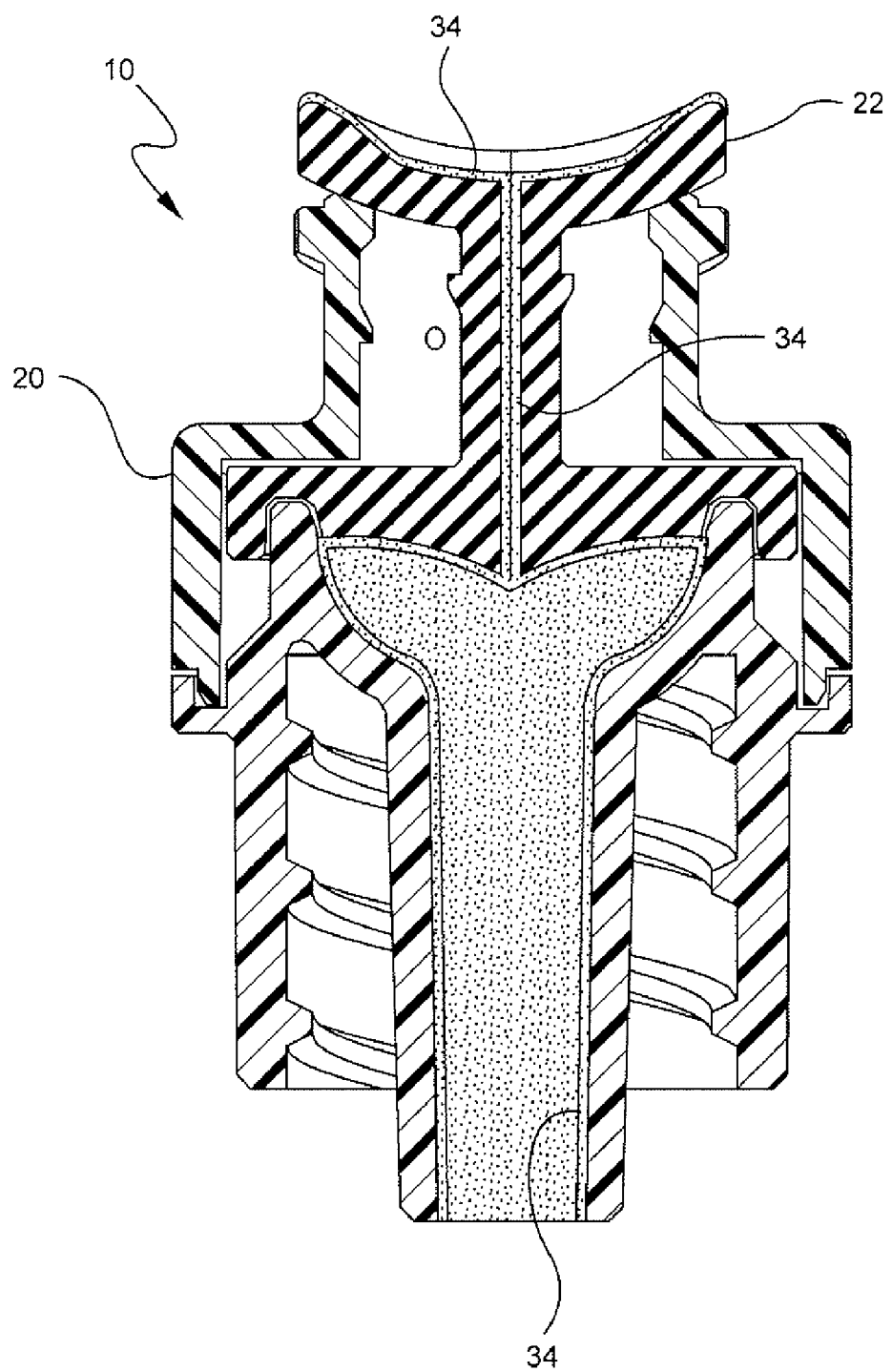
FIG. 2 is a cross section view of a vascular access device having a layer.

Referring now to FIG. 2, vascular access device 10 includes a body 20 that includes a septum 22 within the body 20. The body 20 (including the septum 22) includes a layer 34 that communicates with a pathogenic environment and discourages the adhesion of a pathogen to the layer 34 in order to repress pathogenic activity thereon. The layer 34 resides on, in, or with in any surface, structure, or body of the vascular access device 10 and/or system 28 that is likely to come into contact with a pathogen. The layer 34 is preferably exposed to all surfaces that come into contact with neighboring vascular access devices and with fluid that is infused into the vascular access device 10.

The layer 34 may be constructed of any material capable of discouraging adhesion of a pathogen to the layer 34 in order to repress activity of that pathogen. For example, the layer may include a radio frequency coating that is heated to repress pathogenic activity. The layer 34 may also include a resistive and conductive coating for receiving an electric field. The resistive and conductive coating may be heated by a rapidly oscillating electric field in order to repress pathogenic activity. The resistive and conductive coating may be formed of nickel chrome or a similar alloy or metal. The resistive and conductive coating may be integrated or compounded with any material of the device 10 and/or system 28.

The layer 34 may also include glass, ceramic, small chain polyethylene oxide, polyvinyl alcohol, polylactide, polytetrafluoroethylene, and/or plasma. The layer 34 may also include a glass and/or ceramic that is added to the surface of the device 10 with a plasma energy. The glass and/or ceramic may also be added to the layer 34 and the remainder of the body 20, including the septum 22, such that the glass and/or ceramic is mixed throughout the material of the layer 34, body 20 and septum 22. The layer 34 may also include any substance that is either hydrophobic or hydrophilic and designed to prevent, discourage, or otherwise repress a corresponding pathogen with opposing hydrophilic or hydrophobic properties from forming on the surface of the layer 34. The layer 34 may also include and/or be formed of a microsurface of peaks and valleys that are intentionally spaced to repress pathogenic activity by isolating individual pathogens from contact with other pathogens and pathogen supporting substances. The layer 34 may also include any conventional coating applied to stents that is capable of discouraging adhesion of a pathogen thereto.

Figure 3:
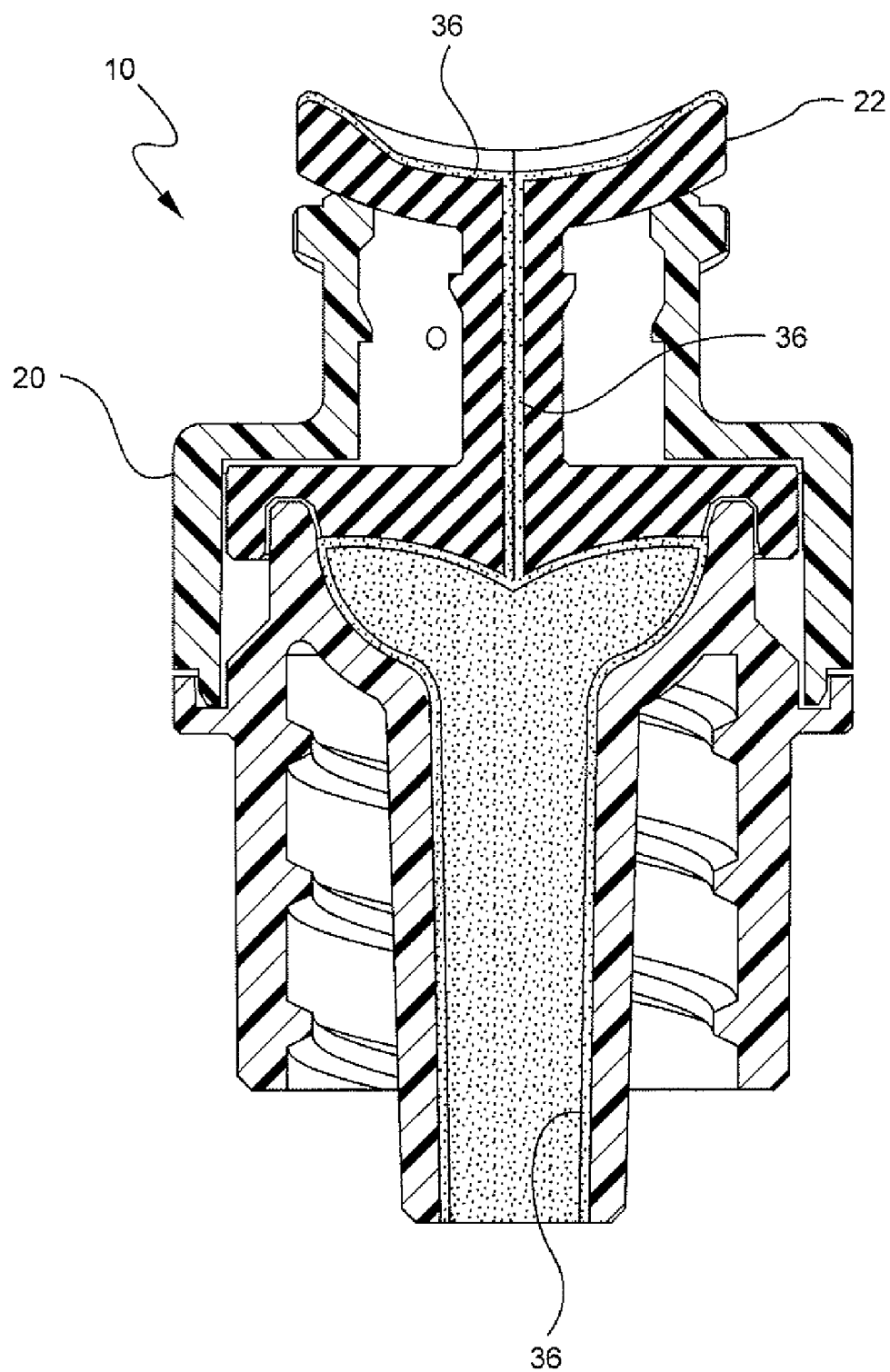
FIG. 3 is a partial cross section view of a vascular access device having a radio frequency layer.

Referring now to FIG. 3, a vascular access device 10 may include a radio frequency activated or energized coating 36 of the body 20, including the septum 22 of the device 10. All fluid path surfaces of the device 10 may be coated, integrated, or compounded with any conductive or other material that has a known radio frequency. The material may be metallic or otherwise suited to receive a radio frequency. A radio frequency generator is then used to transfer or transmit energy to the coating 36, causing the coating 36 to heat up and kill, discharge, or otherwise repress any pathogen adhering to the coating 36.

Figure 4:
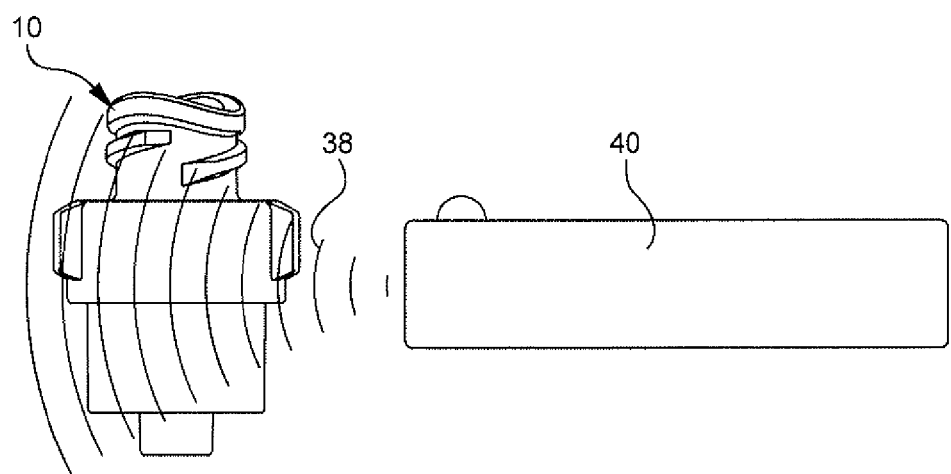
FIG. 4 is a side view of a vascular access device and a radio frequency generator.

Referring now to FIG. 4, the vascular access device 10 is shown receiving radio frequency waves 38 from a radio frequency generator 40. The RF generator 40 may be used to set up a dipole across the device 10 causing both sides of the device 10 to be alternately charged both positively and negatively. By employing a dipole within the device 10, various types of pathogens which respond adversely to positive and/or negative charges will be repressed or otherwise discouraged from residing on the surface of the coating 36.

Figure 5:
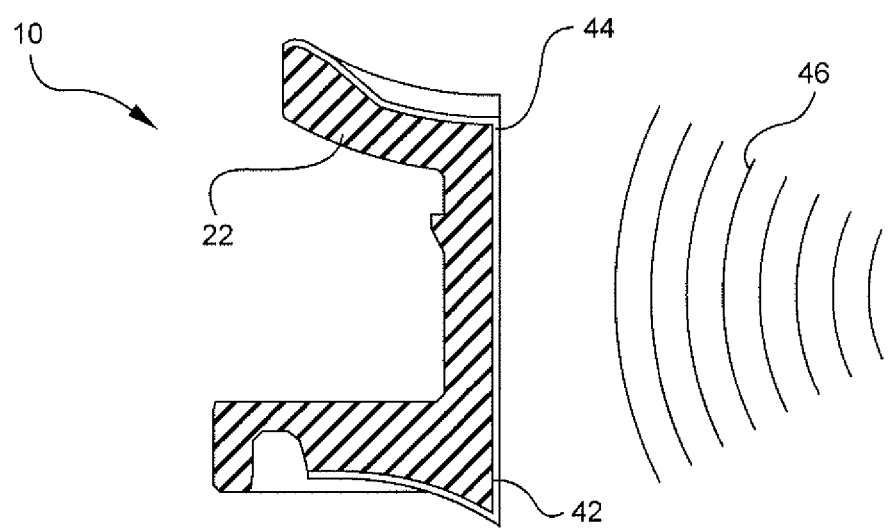
FIG. 5 is a partial cross section view of the septum of a vascular access device having a resistive and conductive coating on the septum.

Referring now to FIG. 5, a vascular access device 10 may include a septum 22 as part of the body 20 of the device 10. The surface 42 of the septum 22 may be coated with a resistive and conductive coating 44 such as nickel chrome. The resistive and conductive coating 44 is capable of receiving energy from an electric field source 46. The coating or film 44 is heated inductively by a rapidly oscillating electric field originating from the electric field source 46. The electric field source 46 may be powered via a primary or rechargeable battery or may be connected to any other conventional source of electricity. When the resistive and conductive coating 44 is heated to a certain temperature, the heat will repress or otherwise discourage a pathogen from residing on the surface 42. The septum 22 may be made of any flexible or other material capable of withstanding high temperatures, such as silicone rubber.

For any of the embodiments described with reference to FIGS. 2 through 5 that provide heat to discourage or repress a pathogen, the heat or other energy source may be provided to the surface as a constant, maintained temperature across at least the material at the surface that discourages a pathogen from ever adhering to the surface in the first place. Thus, a device with an energy source providing a constant supply of heat to at least the surface of the device 10 will prevent the formation of a harmful biofilm on the surface.

Figure 6:
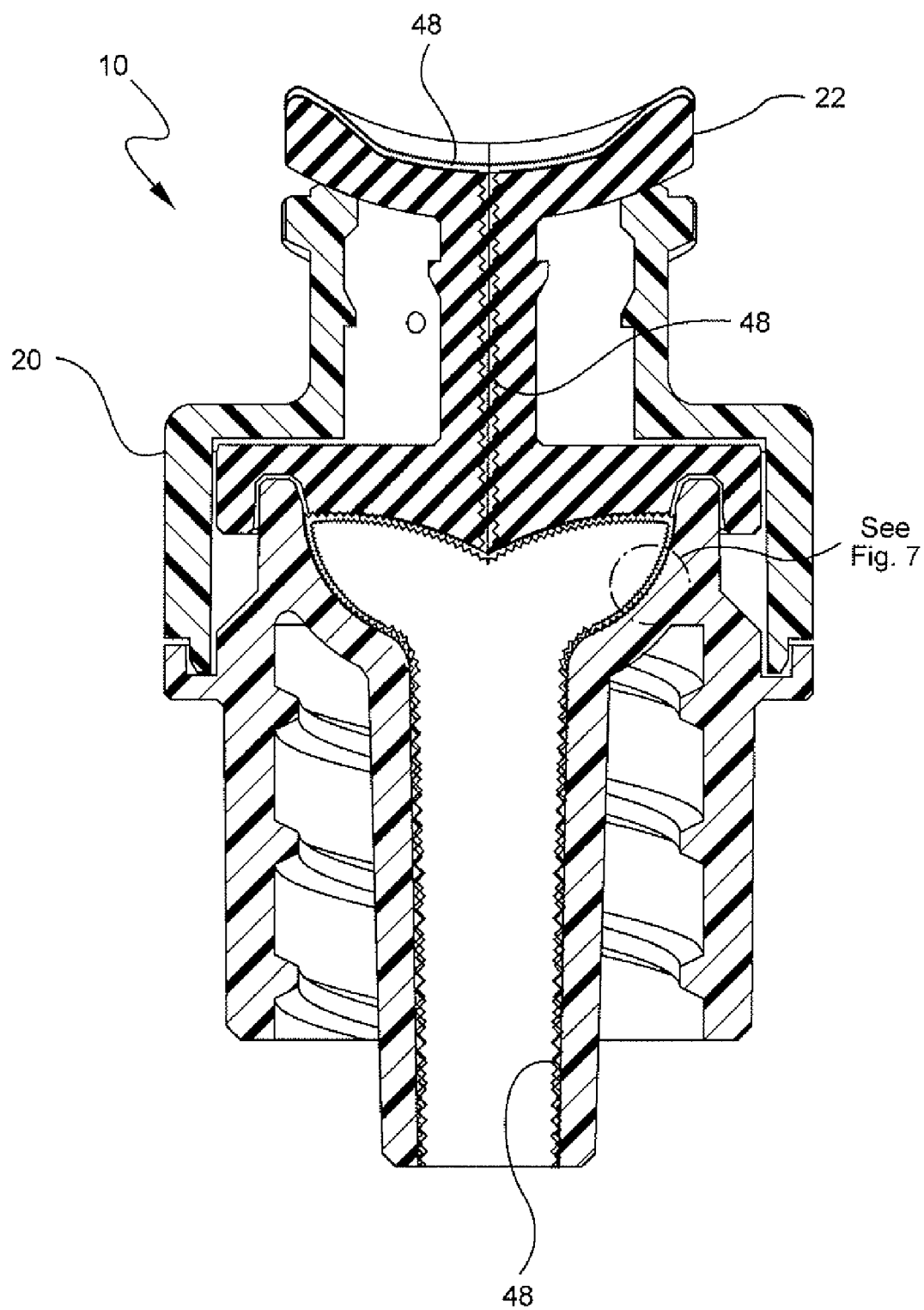
FIG. 6 is a cross section view of a vascular access device with a close-up view of a layer of the vascular access device.
Figure 7:
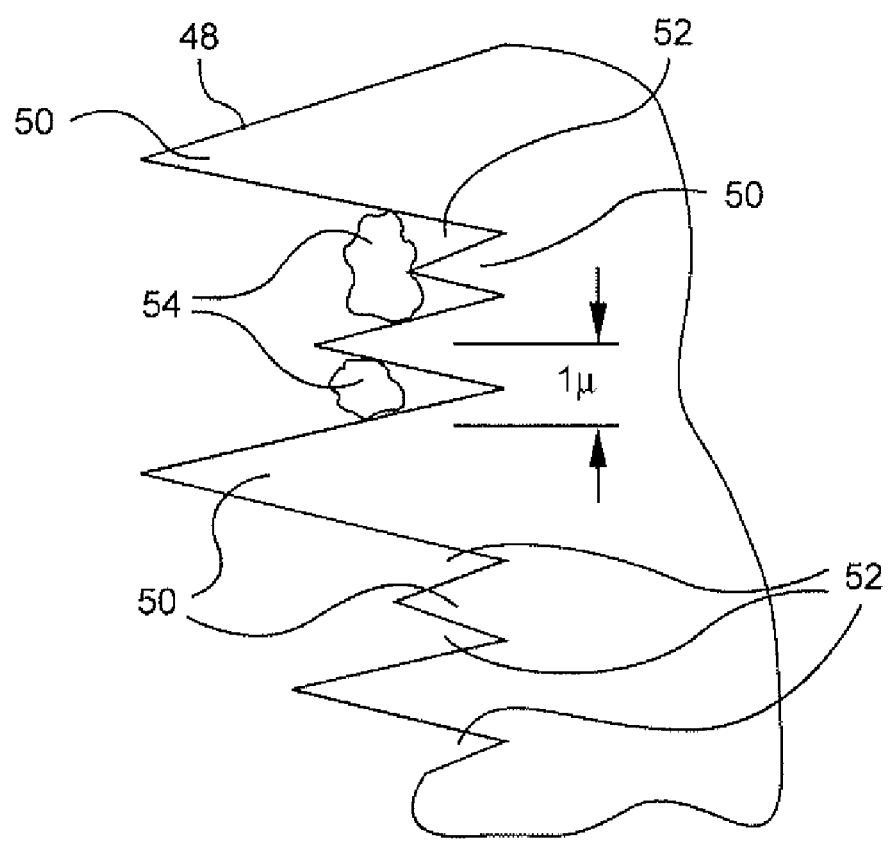
FIG. 7 is a close-up cross sectional view of a portion of the surface illustrated in FIG. 6.

Referring now to FIG. 6, a vascular access device 10 includes a layer 48 that is in contact with or communicates with a pathogenic environment. The layer 48 discourages adhesion of a pathogen to the layer 48 in order to repress pathogenic activity. As shown in FIG. 7, a section of the layer 48 is shown in close-up view to reveal an irregular surface. The irregular surface is a microsurface of peaks 50 and valleys 52 that are strategically spaced in order to repress pathogenic activity. The spacing of the peaks from the valleys is measured depending on the specific type of pathogen 54 that is being repressed.

For example, the space between various peaks 50, or the size of the valleys 52, is large enough to house a pathogen 54 that is one micron in diameter. The valleys 52 provide little more space than one micron in order to isolate each individual pathogen 54 from the other pathogen 54. By isolating pathogens, the peaks 50 and valleys 52 will prevent the communication, organization, proliferation, and development of the pathogens 54 into a harmful biofilm.

The peaks 50 may also be pointed in order to provide a hostile environment to which pathogens 54 may attach. The sharp tip of each peak may thus serve to penetrate through the wall of a pathogen 54, causing death or damage to the pathogen. The spacing, height, and width of the peaks 50 and valleys 52 may be adjusted as required for a particular medical application in order to repress pathogenic activity for specific species of pathogen.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
a vascular access device including a body having a lumen;
a septum positioned within the lumen, the septum having a slit through which a separate extravascular device may be inserted into the vascular access device;
a layer disposed on a surface of the septum, wherein the layer communicates with a pathogenic environment and wherein the layer includes a radio frequency activated coating;
wherein the radio frequency activated coating is metallic and is disposed on the surface of the septum and responds to radio frequency energy by repressing pathogenic activity on the radio frequency activated coating.

2. The medical device of claim 1, wherein the radio frequency activated coating is further disposed on an interior surface of the lumen of the body.

3. The medical device of claim 2, wherein the radio frequency activated coating is further integrated with the interior surface of the lumen of the body.

4. The medical device of claim 2, wherein the radio frequency activated coating is further compounded with the interior surface of the lumen of the body.

5. The medical device of claim 1, wherein the radio frequency activated coating is subject to heating when exposed to a specific radio frequency.

6. The medical device of claim 1, further comprising a radio frequency generator configured to transmit radio frequency waves.

7. The medical device of claim 1, wherein a radio frequency generator is configured to transmit radio frequency waves of a specific radio frequency known to induce heating of the radio frequency activated coating.

8. A medical device, comprising:
means for accessing a vascular system of a patient, and
means for discouraging adhesion of a pathogen,
wherein the pathogen resides near the means for accessing a vascular system of a patient,
wherein the means for accessing a vascular system includes a body having a lumen and a split septum positioned within the lumen, through which a separate extravascular device may be inserted into the means for accessing a vascular system, having a layer disposed on a surface of a septum wherein the layer includes a radio frequency activated coating,
wherein the radio frequency activated coating is disposed on the surface of the septum, the radio frequency activated coating responding to radio frequency energy by repressing pathogenic activity on the radio frequency activated coating, and wherein the radio frequency activated coating is metallic.

9. A medical system, comprising:
a vascular access device including a body having a lumen;
a septum positioned within the lumen, the septum having a slit through which a separate extravascular device may be inserted into the vascular access device;
a radio frequency activated coating included in an interior surface of the lumen of the body, the radio frequency activated coating being metallic and being subject to heating when exposed to a specific radio frequency; and a radio frequency generator configured to transmit radio frequency waves of the specific radio frequency.

10. The medical device of claim 9, wherein the radio frequency activated coating is further integrated with the interior surface of the lumen of the body.

11. The medical device of claim 9, wherein the radio frequency activated coating is further compounded with the interior surface of the lumen of the body.

12. The medical device of claim 9, wherein the radio frequency activated coating is further disposed on or within the septum.

* * * * *